(12) United States Patent
Pallikaris et al.

(10) Patent No.: US 10,548,719 B2
(45) Date of Patent: Feb. 4, 2020

(54) DEVICES FOR RECONSTRUCTION OF A LENS CAPSULE AFTER CATARACT SURGERY

(71) Applicants: Ioannis Pallikaris, Crete (GR); Onurcan Sahin, Istanbul (TR)

(72) Inventors: Ioannis Pallikaris, Crete (GR); Onurcan Sahin, Istanbul (TR)

(73) Assignee: EYE-PCR B.V., Amsterdam (NL)

( * ) Notice: Subject to any disclaimer, the term of this patent is extended or adjusted under 35 U.S.C. 154(b) by 0 days.

(21) Appl. No.: 15/446,121

(22) Filed: Mar. 1, 2017

(65) Prior Publication Data

US 2018/0250124 A1 Sep. 6, 2018

(51) Int. Cl.
  *A61F 2/16* (2006.01)
(52) U.S. Cl.
  CPC ...... *A61F 2/1694* (2013.01); *A61F 2002/169* (2015.04); *A61F 2002/1682* (2015.04);
  (Continued)
(58) Field of Classification Search
  CPC ............ A61F 2/1694; A61F 2002/1682; A61F 2002/16901; A61F 2002/0091; A61F 2002/169; A61F 2002/16902
  See application file for complete search history.

(56) References Cited

U.S. PATENT DOCUMENTS 4,710,194 A   12/1987  Kelman
5,824,074 A * 10/1998  Koch .................... A61F 2/1648
                                                       623/6.34
(Continued)

FOREIGN PATENT DOCUMENTS

EP           507292 B1      7/1997
JP    WO 2015087930 A1  *  6/2015  ........... A61F 2/1635
                    (Continued)

OTHER PUBLICATIONS

Oliver Findl, Wolf Buehl, Rupert Menapace, Michael Georgopoulos, Georg Rainer, Hannes Siegl, Alexandra Kaider, Axel Pinz, Comparison of 4 methods for quantifying posterior capsule opacification. (2003) J Cataract Refract Surg. 29 (1):106-11.

(Continued)

*Primary Examiner* — David H Willse
*Assistant Examiner* — Javier G Blanco
(74) *Attorney, Agent, or Firm* — Benjamin Aaron Adler (57) ABSTRACT

Provided herein are devices used to reconstruct a natural lens capsule after a cataract surgery. The device flexibly adapts to the tension of the lens capsule as it is relaxed or contracted. This device comprises a ring-shaped rigid component. The rigid component comprises a distal end in contact with an anterior surface of the capsule and a proximal end disposed on a posterior surface of the capsule and disposed against a Wieger's ligament of the eye. A ring-shaped flexible component substantially concentric with the rigid component is flexibly fitted against an inner surface of the capsule. The ring-shaped flexible component comprises a proximal end formed on an outer surface of a proximal end of the rigid component, and a distal end extending away from the rigid component. A groove is disposed on an inner surface of the rigid component configured to receive haptics on an intraocular lens.

13 Claims, 5 Drawing Sheets

(52) U.S. Cl.
CPC ............... *A61F 2002/16901* (2015.04); *A61F 2002/16902* (2015.04); *A61F 2220/0025* (2013.01); *A61F 2250/0097* (2013.01)

(56) References Cited

U.S. PATENT DOCUMENTS

| | | | |
|---|---|---|---|
| 6,063,118 A * | 5/2000 | Nagamoto | A61F 2/16 128/898 |
| 8,636,796 B2 | 1/2014 | Josephine et al. | |
| 9,339,375 B2 | 5/2016 | Lee et al. | |
| 2005/0085907 A1 | 4/2005 | Hanna | |
| 2005/0209692 A1 | 9/2005 | Zgang | |
| 2006/0047339 A1 | 3/2006 | Brown | |
| 2008/0281413 A1* | 11/2008 | Culbertson | A61F 2/16 623/6.12 |
| 2009/0018650 A1 | 1/2009 | Boxer Wachler | |
| 2010/0204790 A1 | 8/2010 | Whitsett | |
| 2010/0228344 A1 | 9/2010 | Shadduck | |
| 2011/0082543 A1 | 4/2011 | Soll et al. | |
| 2013/0304206 A1* | 11/2013 | Pallikaris | A61F 2/1651 623/6.43 |
| 2015/0366656 A1* | 12/2015 | Wortz | A61F 2/1624 623/6.22 |

FOREIGN PATENT DOCUMENTS

| | | |
|---|---|---|
| RU | 2330634 C2 | 8/2008 |
| RU | 2459598 C2 | 8/2012 |
| WO | 2007044604 A1 | 4/2007 |
| WO | 2008108523 A1 | 9/2008 |

OTHER PUBLICATIONS

Ilias Georgalas, Petros Petrou, George Kalantzis, Dimitrios Papaconstantinou, Chrysanthi Koutsandrea, Ioannis Ladas. Nd:YAG capsulotomy for posterior capsule opacification after combined clear corneal phacoemulsification and vitrectomy. (2009) Ther Clin Risk Manag. 5:133-137.

Daniel Goldberg, Computer-animated model of accommodation and theory of reciprocal zonular action. (2011). Clin Ophthalmol. 5:1-7.

* cited by examiner

DEVICES FOR RECONSTRUCTION OF A LENS CAPSULE AFTER CATARACT SURGERY

BACKGROUND OF THE INVENTION

Field of the Invention

The present invention relates to the fields of ophthalmology and surgical devices for operations on the eye. More specifically, the present invention relates to a device for functional and anatomical reconstruction of human lens capsules and for precise placement of an intraocular lenses for any surgery that requires replacement and alignment of the crystalline lens.

Description of the Related Art

An intraocular lens is a plastic lens that has substantially the same optical power as a natural lens it is intended to replace. Typically, during a cataract surgery, an ophthalmic surgeon removes a cataract impaired natural lens and replaces it with an artificial intraocular lens. There are generally three types of intraocular lenses including refractive lenses, diffractive lenses, and refractive-diffractive lenses. A refractive lens converges light towards a focal point on the optical axis by refraction, while a diffractive lens creates a diffraction pattern forming one focal point on the optical axis per diffraction order. A refractive-diffractive lens combines the features of both types. However, these purely refractive bi- or multi-focal lenses have some notable drawbacks. Firstly, their effectiveness is heavily dependent on the size and the centration of the pupil. Secondly, because they have several focal points, the resulting contrast is reduced. This may induce the formation of halos, in particular, in far vision, with reduced luminosity (see, for example, U.S. Pat. No. 8,636,796 B2).

Moreover, posterior capsule opacification (PCO or after cataract) remains a common problem after cataract surgery with implantation of an intraocular lens. Posterior capsule opacification generally results from the transition from intracapsular cataract extraction (ICCE) to extracapsular cataract extraction (ECCE), where the posterior lens capsule is left intact during surgery. Patients with posterior capsule opacification suffer from decreased visual acuity, impaired contrast sensitivity, and glare disability. Clinically, components of posterior capsule opacification are identified as a regeneratory component and a fibrotic component with a regeneratory posterior capsule opacification component much more common than the fibrotic component.

Regeneratory posterior capsule opacification results from residual lens epithelial cells (LECs) from the lens equator region, the so-called E-cells, migrating and proliferating into the space between the posterior capsule and the intraocular lens and forming layers of lens material and Elschnig pearls. In contrast, fibrotic posterior capsule opacification is caused by LECs from the anterior capsule that undergoe transformation to myofibroblasts and gain access to the posterior capsule, causing whitening and wrinkling of the capsule. This can lead to decentration of the intraocular lens and hinder visualization of the peripheral retina. Findl et al. (J Cataract Refract Surg 2003; 29(1):106-11) disclose that both components of posterior capsule opacification lead to a decrease in visual function when they affect the central region around the visual axis. A YAG or Nd laser, utilized in a YAG laser capsulotomy, is most commonly used to treat posterior capsule opacification. However, as disclosed in Georgalas et al. (Ther Clin Risk Manag. 2009; 5:133-137) laser capsulotomy may lead to other complications, such as retinal detachment or intraocular pressure rise.

European Patent No. 507292 B1 describes the need of an "inhibiting device" for keeping the shape of the capsular bag substantially circular after a cataract extraction and inhibiting issues such as invasion of metamorphosed epithelial cells into a posterior capsular bag and further to inhibiting device wherein an intraocular lens can be retained in good state by forming a groove in the inner periphery thereof. He describes a steady circular shape of the device effective to inhibit capsular shrinking without referring to the actual diameter of the outer part of the ring.

US Publication No. 2006/0047339 A1 describes a device attached to natural lens capsule such that the lens capsule may be maintained in a configuration to avoid postoperative changes that are deleterious to vision. Single or dual optics system is provided, which may be accommodating. The role of the "postoperative contraction" of the empty capsule, in the displacement of the lens, resulting in optical changes and in induced astigmatism is emphasized. Therefore, there is a need to provide a device or apparatus and procedure to maintain the form of the lens capsule and to maintain the diameter a capsulotomy opening for the device.

International Application No. WO2007044604 A1 describes the "spatial relationship of structures within the eye, such as the distance from the a surface of the cornea to a posterior surface of the crystalline lens capsule and from the cornea or the posterior surface of the lens capsule" to the retina is measured preoperatively, for example by using ultrasound, partial coherence interferometry, optical coherence tomography or laser measuring techniques or by any other means known to the art, thus establishing the preoperative anatomical relationships. A surgical procedure, such as an intraocular lens implantation is performed and spacing means are provided to restore those premeasured spatial relationships or a predetermined new spacing. The spacing means may include, for example spacers, rings, inflatable structures or thick or multiple lenses. These means help with maintaining the normal depth of the patient's anterior and posterior capsule and prevent forward movement of the vitreous and retinal detachment that may occur as a result of such movement.

Goldberg (Clin Ophthalmol. 2011; 5:1-7) states that "the crossing zonules cradle, shape stabilize the posterior lens. In the model, the anterior vitreous zonule is inserted in the Wieger's ligament, and the PIZ-LE zonule anchors the lens equator to the posterior insertion zone. The crossing zonules and Wieger's ligament maintain lens placement while the anterior and posterior zonules provide reciprocal accommodation and disaccommodation. Wieger's ligament representing the mid-peripheral zone of the posterior capsule is the most important area for stabilizing the lens position during the accommodation.

US Publication No. 2010/0204790 A1 describes an intraocular lens device having a ring shape fixation platform, which can create a "frame" in which the intraocular lens of the present invention can be attached . . . and conclude the discovery of the present invention makes possible a surgical method for insertion and subsequent removal and exchange of an intraocular lens with reduced risk of injury to the eye or loss of sight.

Based on the Market Scope Report (2015 Comprehensive Report on the Global Intraocular Lens Market, June 2015), the premium intraocular lens market is going to reach the 9.3% of the global number and the 34% of the total revenues of the global intraocular lens market. The multifocal and Toric IOLs will dominate the premium intraocular lens market at the market share of almost 90%. Toric and multifocal are very sensitive to the exact centration and positioning inside the capsule.

Several patents and publications, including U.S. Pat. No. 9,339,375 B2, U.S. Pat. No. 4,710,194, US Publication No. 2005/0085,907, US Publication No. 2005/0209692, US Publication No. 2010/0204790, US Publication No. 2010/0228344, US Publication No. 2011/0082543 and European Application No. 037,390A2, disclose a variety of intracapsular rings for different purposes. However, these works describe rings that either have one standard size or a variety of sizes without any adjustability for accommodation. These devices generally comprise a ring and an optical system adapted to the ring. Some of the devices comprise a deformable ring that under the pressure of the ciliary body changes the shape of the central optical part and mimics an accommodation mechanism.

None of the previous works in the field take into consideration the modern theory of accommodation and the preservation of continuous change of the shape of the capsule, due to the complexity of zonular traction regarding the multifocal and toric intraocular lens, which are already in the market and expected to improve rapidly in the near future. Therefore, there is a recognized need in the art for a device and method for reconstructing the capsule. Particularly, the prior art is deficient in devices that enable precise placement and alignment of the intraocular lens post-surgically. The present invention fulfills this long-standing need and desire in the art.

SUMMARY OF THE INVENTION

The present invention is directed to a device for reconstructing a natural lens capsule of an eye after a cataract surgery. The device comprises a ring-shaped rigid component. The rigid component comprises a distal end in contact with an anterior surface of the capsule and a proximal end disposed on a posterior surface of the capsule and against a Wieger's ligament in the eye. A ring-shaped flexible component substantially concentric with the rigid component is flexibly fitted against an inner surface of the capsule. The ring-shaped flexible component comprises a proximal end formed on an outer surface of the proximal end of the rigid component, and a distal end extending away from the rigid component. A groove is disposed on an inner surface of the rigid component configured to receive haptics on an intraocular lens. The present invention is directed to a related device further comprising a ledge formed from a top of the distal end of the rigid component.

The present invention also is directed to a device for flexibly restoring tension for a natural lens capsule after a cataract surgery. The device comprises a ring-shaped rigid component comprising a distal end disposed in supporting relationship with an anterior surface of the lens capsule, a proximal end disposed in supporting relationship with a posterior surface of the lens capsule and disposed against a Wieger's ligament of the eye, and a ledge formed from a top of the distal end of the rigid component. A ring-shaped flexible component substantially concentric with the rigid component is flexibly fitted against an inner surface of the capsule. The flexible component is configured to flex away from the rigid component when ciliary muscles are relaxed and zonules are tense, and flex toward the rigid component when the ciliary muscles are contracted and the zonules are relaxed. The ring-shaped flexible component comprises a proximal end formed on an outer surface of the proximal end of the rigid component, and a distal end extending away from the rigid component. A groove is disposed on an inner surface of the rigid component, configured to receive haptics on an intraocular lens. The present invention is directed to a related device further comprising a plurality of markers disposed on a top surface of the ledge configured to guide toric lens alignment. The present invention is directed to another related device further comprising a plurality of gaps disposed around a circumference of said ring-shaped flexible component configured to improve flexibility thereof.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

As used herein, the following terms and phrases shall have the meanings set forth below. Unless defined otherwise, all technical and scientific terms used herein have the same meaning as commonly understood to one of ordinary skill in the art.

As used herein, the term, "a" or "an" may mean one or more. As used herein in the claim(s), when used in conjunction with the word "comprising", the words "a" or "an" may mean one or more than one. As used herein "another" or "other" may mean at least a second or more of the same or different claim element or components thereof. The terms "comprise" and "comprising" are used in the inclusive, open sense, meaning that additional elements may be included.

As used herein, the term "or" in the claims refers to "and/or" unless explicitly indicated to refer to alternatives only or the alternatives are mutually exclusive, although the disclosure supports a definition that refers to only alternatives and "and/or".

As used herein, the term "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As used herein, the term "distal end" refers to an end that is away from the posterior surface of the capsule; the term "proximal end" refers to an end that is toward the posterior surface of the capsule.

In one embodiment of the present invention, there is provided a device for reconstructing a natural lens capsule of an eye after a cataract surgery, comprising a ring-shaped rigid component comprising: a distal end in contact with an anterior surface of the capsule; and a proximal end disposed against a Wieger's ligament in the eye; a ring-shaped flexible component substantially concentric with the rigid component and flexibly fitted against an inner surface of the capsule, comprising: a proximal end formed on an outer surface of the proximal end of the rigid component; and a distal end extending away from the rigid component; and a groove disposed on an inner surface of the rigid component configured to receive haptics on an intraocular lens.

Further to this embodiment the device further may comprise a ledge formed from a top of the distal end of the rigid component. In this further embodiment, the ledge may comprise a plurality of markers disposed on a top surface thereof, configured to guide a toric lens alignment. Also in this further embodiment the ledge may have a width of about 0.1 mm to about 1 mm wide.

In both embodiments, the proximal end of the rigid component may have a thickness of about 0.2 mm to about 1 mm. Also, the distal end of the rigid component may have a thickness of about 0.1 mm to about 0.5 mm. In addition, the rigid component may be made of or may comprise, but are not limited to, silicon, acryl, poly(methyl methacrylate), hydrogel, or a combination thereof.

Also in both embodiments, the ring-shaped rigid component may be substantially perpendicular to the anterior surface of the natural lens capsule. In both embodiments the ring-shaped flexible component may be configured to flex away from the rigid component, when ciliary muscles are relaxed and zonules are tense, and to flex toward the rigid component, when the ciliary muscles are contracted and the zonules are relaxed.

Further to both embodiments, the ring-shaped flexible component may comprise a plurality of gaps disposed around a circumference thereof. Also, the gaps each may have a width of about 0.1 mm to about 5 mm. In addition, the ring-shaped flexible component may have a thickness of about 0.05 mm to about 0.75 mm. Furthermore, the ring-shaped flexible component may be made of or may comprise, but are not limited to, silicon, acryl, poly(methyl methacrylate), hydrogel, or a combination thereof. Further still in this embodiment, the ring-shaped rigid component and the ring-shaped flexible component form an angle of about 2 degree to about 90 degree when fitted inside the natural lens capsule.

In another embodiment of the present invention, there is provided a device for flexibly restoring tension for a natural lens capsule after a cataract surgery, comprising: a ring-shaped rigid component comprising: a distal end disposed in a supporting relationship with an anterior surface of the capsule and; a proximal end disposed in a supporting relationship with an posterior surface of the capsule and disposed against a Wieger's ligament of the eye; and a ledge formed from a top of the distal end of the rigid component; a ring-shaped flexible component substantially concentric with the rigid component and flexibly fitted against an inner surface of the capsule, configured to flex away from the rigid component when ciliary muscles are relaxed and zonules are tense, and flex toward the rigid component when the ciliary muscles are contract and the zonules are relaxed, the flexible component comprising: a proximal end formed on an outer surface of the proximal end of the rigid component; and a distal end extending away from the rigid component; and a groove disposed on an inner surface of the rigid component configured to receive haptics on an intraocular lens.

Further to this embodiment, the device may comprise a plurality of markers disposed on a top surface of the ledge configured to guide toric lens alignment. In another further embodiment the device may comprise a plurality of gaps disposed around a circumference of the ring-shaped flexible component configured to improve flexibility thereof. In this further embodiment, the gaps each may have a width of about 0.1 mm to about 5 mm wide.

In all embodiments, the ledge may have a width about 0.1 to about 1 mm. Also, the proximal end of the rigid component may have a thickness of about 0.2 mm to about 1 mm and the distal end of the rigid component may have a thickness of about 0.1 mm to about 0.5 mm. In addition the ring-shaped rigid component may be made of or may comprise, but are not limited to, silicon, acryl, poly(methyl methacrylate), hydrogel, or a combination thereof. Furthermore, the ring-shaped rigid component may be substantially perpendicular to the anterior surface of the natural lens capsule. Further still, the ring-shaped rigid component and the ring-shaped flexible component form an angle of about 2 degrees to about 90 degrees when disposed inside the natural lens capsule.

Provided herein are devices for reconstruction of the capsule 1 after a cataract surgery. As described below, the invention provides a number of advantages and uses, however such advantages and uses are not limited by such description. Embodiments of the present invention are better illustrated with reference to the Figure(s), however, such reference is not meant to limit the present invention in any fashion. The embodiments and variations described in detail herein are to be interpreted by the appended claims and equivalents thereof.

Figure 1:
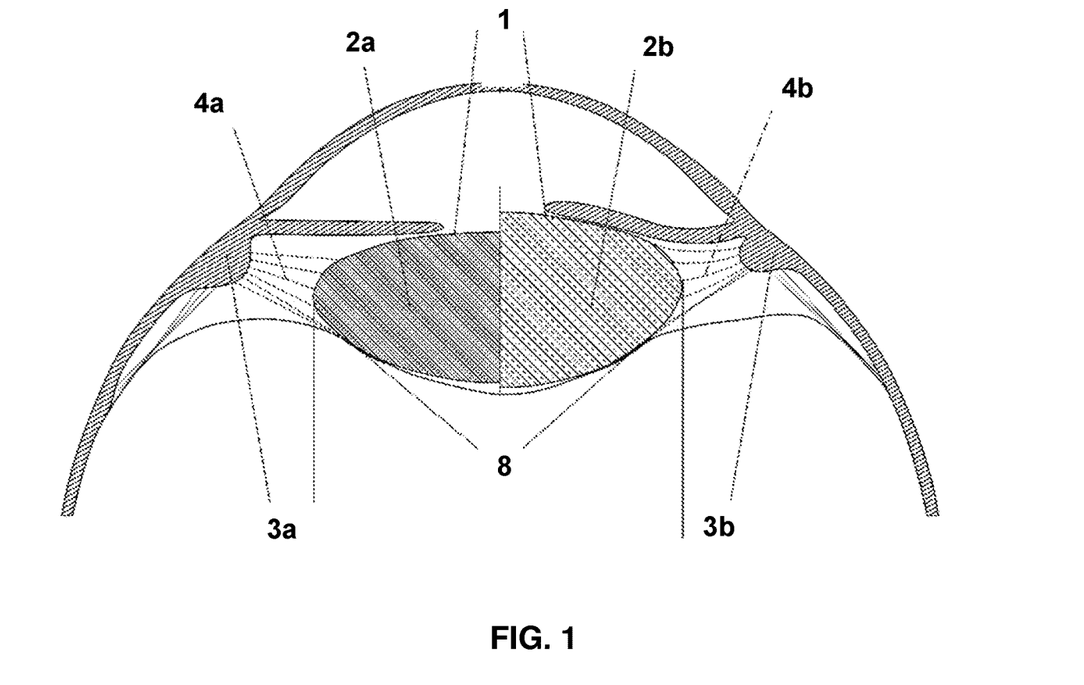
FIG. 1 depicts the structure of a capsule and Wieger's ligament with (left side) and without (right side) contraction of ciliary body.

As shown in FIG. 1, the lens of the eye within the natural lens capsule 1 switches between flattened 2a or convex 2b when the ciliary muscles relax or contract to adjust vision focus. More specifically, when an eye is looking at objects at a far distance, the ciliary muscles are relaxed 3a and the zonules 4a are tensed, resulting in the lens being flattened. When the ciliary muscles are contracted 3b and the zonules are relaxed 4b, the lens of the eye is in a convex shape 2b, providing more refractive power. Therefore, a concentric ring-shaped device 5 is used to accommodate the flexibility of the dynamic structure of an eye.

Figure 2:
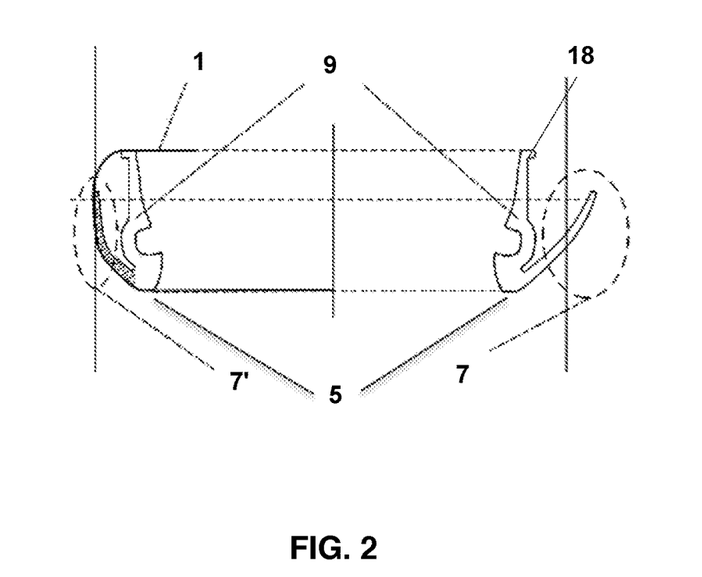
FIG. 2 is a cross sectional view of the device showing the flexible component of the device in free form (right side) and fitted against the side surface of a capsule of an eye (left side).

As shown FIG. 2, the device has a V-shaped cross-sectional surface. The device comprises a rigid component 9 and a flexible or deformable component 7 (without tension) or 7' (with tension) disposed outside of or posterior to the rigid component. A proximal end of the flexible component is formed at the outer surface of at the proximal end of the rigid component. When it is placed in the natural lens capsule 1, the rigid component 9 supports the lens capsule while the flexible component 7' fits against and contacts the side surface of the lens capsule, configured to contract or relax with the contraction or relaxation of the capsule. Generally, the rigid component may be perpendicular to the anterior surface of the lens capsule.

Figure 3:
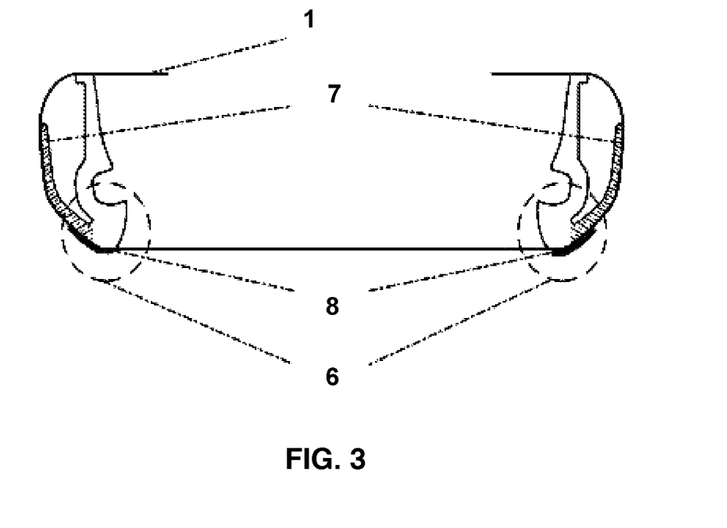
FIG. 3 is a cross sectional view of the device showing the proximal end of the device is disposed in the capsule and against Wieger's ligament.

FIG. 3 illustrates that when the device is placed into the natural lens capsule, the proximal end of the rigid component is disposed against Wieger's Ligament 8. The outer surface of the flexible component is in direct contact with the inner surface of the capsule. The flexible component is under constant pressure from the capsule. It blocks any fibroblast and lens epithelial cells migrating to the posterior capsule. Preferably, the angle between the rigid component and the flexible component is about 0 degrees to about 90 degrees when the capsule contracts and relaxes. The rigid component and the flexible component individually may be made of biocompatible materials, such as, but not limited to, silicon, an acrylic, such as poly(methyl methacrylate), hydrogel or a combination thereof. The thickness of the rigid and flexible components define the parameters of flexibility and rigidity.

Figure 4:
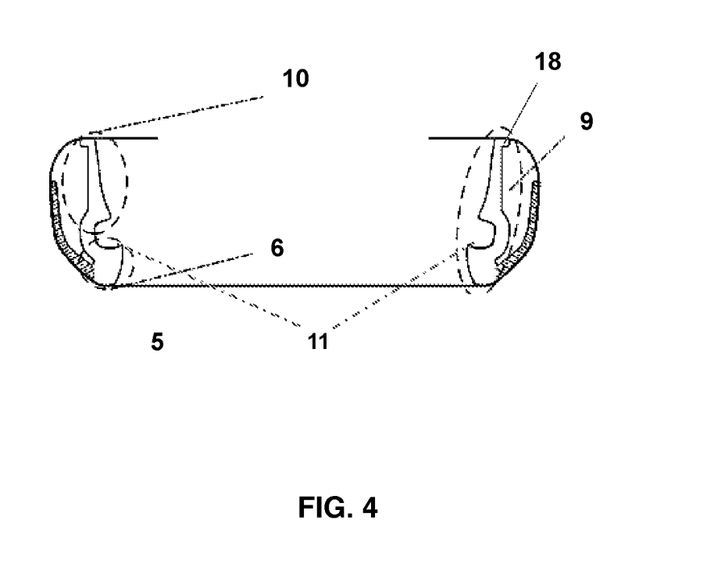
FIG. 4 is a cross sectional view of the device showing the diameter of the anterior surface of the capsule is greater than the posterior surface thereof.

As shown in FIG. 4, the top portion 10 of the rigid component, which is in contact with the anterior of the capsule, is thinner than the bottom portion 6 thereof, which is in contact with the posterior of the capsule. A ledge 18 is formed at the distal end of the top portion of the rigid component. The diameter of the top portion 10 of the rigid component may be greater than or substantially the same as that of the bottom portion 6 thereof. This conical-like shape of the rigid component creates a better visual field for surgeons and allows them to see the groove 11 during the eye surgery, providing easy access for placing and aligning the lens 13. Preferably, the thickness of the rigid component may be from 0.1 mm to 1 mm. The thickness of the flexible component may be from 0.05 mm to 0.75 mm.

Figure 5:
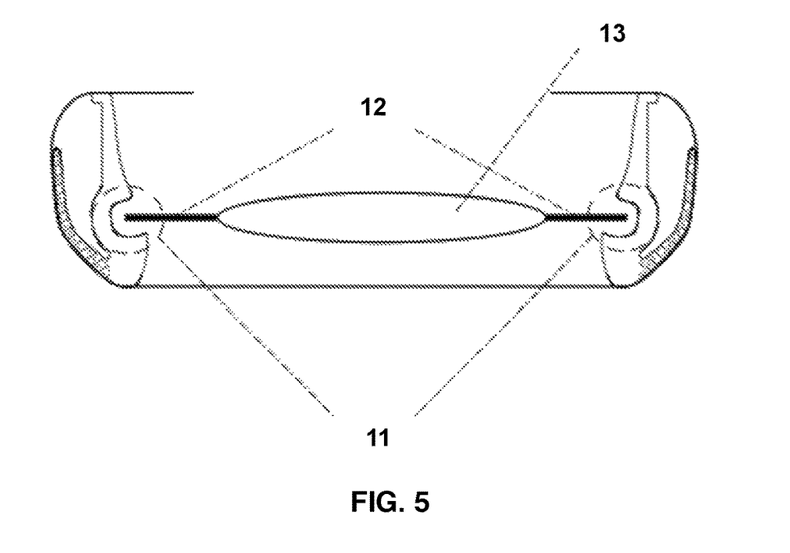
FIG. 5 is a cross sectional view of the device showing an intraocular lens is placed in the device by inserting the haptics thereof into a groove disposed on the inner surface of the rigid component.

FIG. 5 illustrates that a ring-shaped groove 11 is disposed on the inner surface of the rigid component and is configured to fit or receive and to secure the haptics 12 on the intraocular lens. The groove 11 keeps the lens well aligned in the center of the capsule. Once the haptics 12 on the lens 13 are placed in the groove 11, the groove 11 removably secures the haptics 12 and prevents the lens 13 from tilting or twisting.

Figure 6:
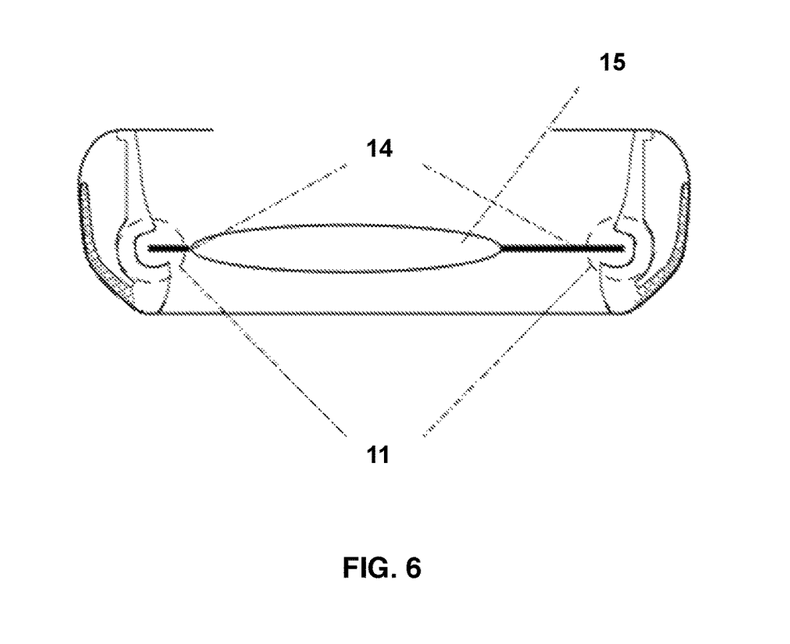
FIG. 6 is a cross sectional view of the device showing an asymmetric intraocular lens is placed in the device.

FIG. 6 shows that an intraocular lens with asymmetric haptics 14 is placed into the ring-shaped groove 11. This is used to fit premium intraocular lens in a patient's eye with higher angle kappa, in case of a pupil eccentricity in regards to the optical axis, where this eccentricity is greater than 0.2 mm.

Figure 7:
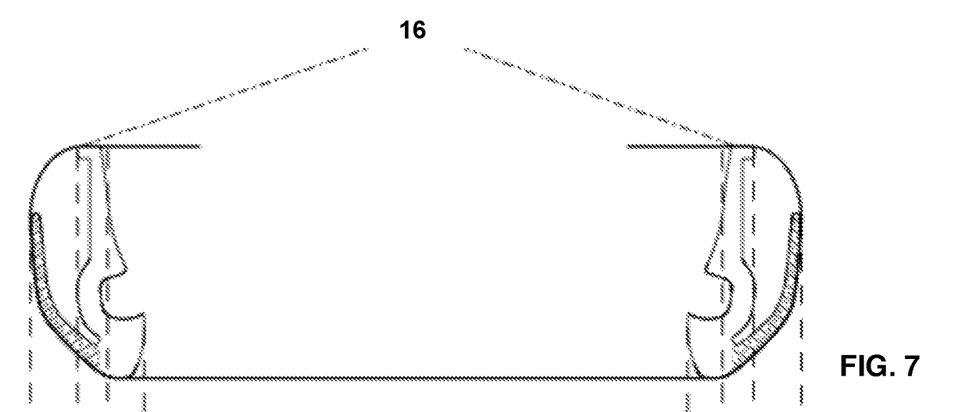
FIG. 7 is a cross sectional view from the side of the device showing the rigid component and the flexible component.
Figure 8:
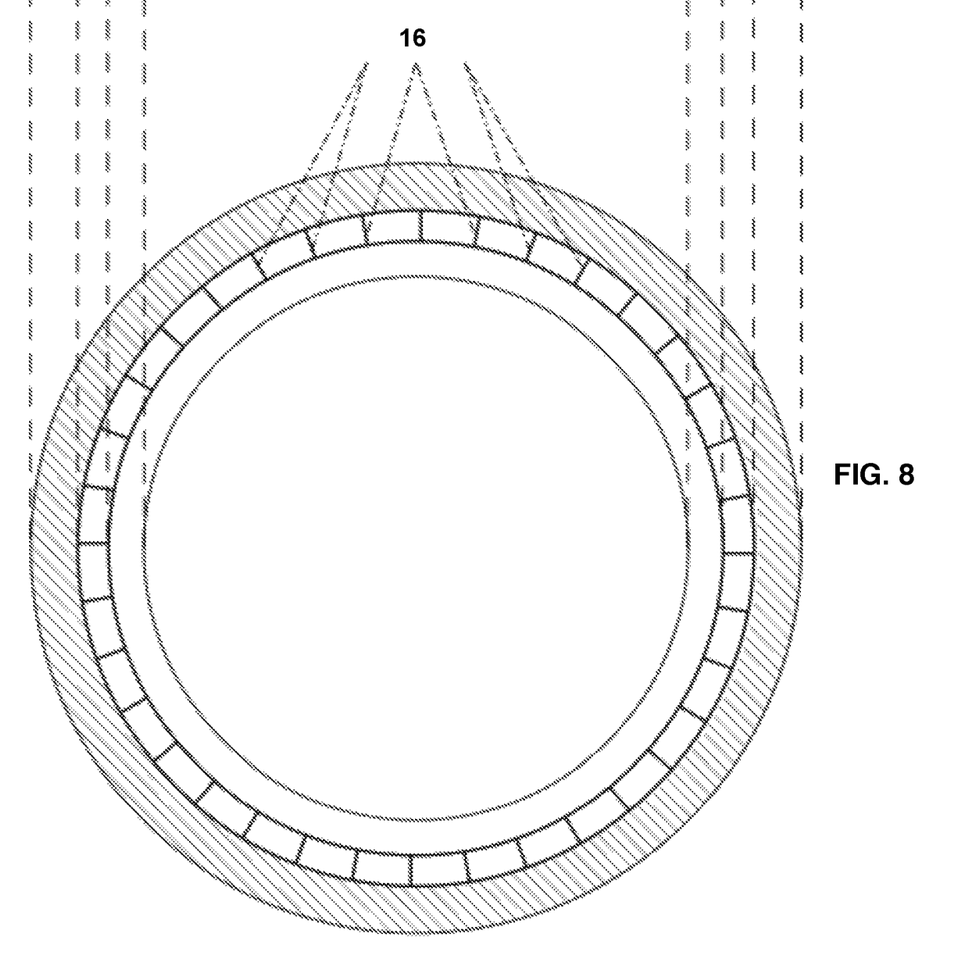
FIG. 8 is a top view of the device showing a plurality of markers as the indicators for toric intraocular lens alignment is disposed on the top surface of the rigid component.

FIG. 7 and FIG. 8 illustrate the corresponding parts in a side view shown in and a top view, respectively, of the device. Particularly, FIG. 8 shows a plurality of markers 16 disposed on the top surface of the ledge formed on the rigid component.

Figure 9:
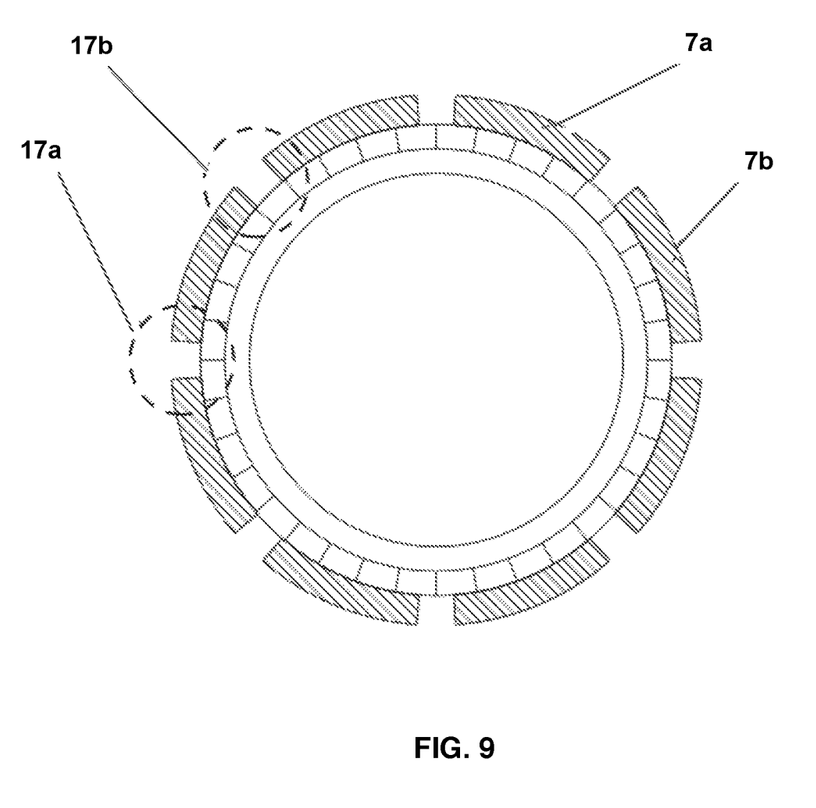
FIG. 9 is a top view of the device showing a plurality of gaps disposed along the circumference of the flexible component to improve the flexibility thereof.

In FIG. 9 a plurality of gaps, as represented by 17a and 17b, is disposed along the circumference of the flexible component to improve the flexibility thereof. These gaps divide the flexible component into plurality of discontinuous sections, as represented by 7a and 7b.

The present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. Also, the terms in the claims have their plain, ordinary meaning unless otherwise explicitly and clearly defined by the patentee.

What is claimed is:

1. A prosthetic capsular device for reconstructing a natural lens capsule of an eye after a cataract surgery, the device comprising a housing configured to receive an intraocular lens (IOL), the housing consisting of:
   a ring-shaped rigid component comprising:
      a distal end with a thickness of about 0.1 mm to about 0.5 mm, the distal end sized and configured to contact an anterior surface of the natural lens capsule;
      an anterior central opening defined at said distal end, the anterior central opening having a perimeter capable of allowing insertion of an intraocular lens;
      a ledge formed from a top of the distal end, the ledge comprising a capsular-engaging top surface;
      a plurality of markers disposed on said top surface of the ledge;
      a proximal end with a thickness of about 0.2 mm to about 1 mm, the proximal end comprising a capsular-engaging surface sized and configured to be disposed in a supporting relationship with a posterior surface of the natural lens capsule and configured to be disposed against a Wieger's ligament in the eye; and
      a circumferential wall extending from said proximal end to said distal end;
   a ring-shaped flexible component substantially concentric with said rigid component with a thickness of about 0.05 mm to about 0.75 mm that is less than the thickness of the distal end of the rigid component or the thickness of the proximal end of the rigid component, the ring-shaped flexible component defining a capsular-engaging circumferential wall sized and configured to flexibly fit against an inner surface of the natural lens capsule, said ring-shaped flexible component comprising:
      a proximal end formed on an outer surface of the proximal end of the rigid component;
      a distal end extending anteriorly and away from said rigid component, said distal end being a free end; and
      a plurality of gaps disposed around a circumference of the flexible component; and
   a groove formed on an inner surface of the rigid component configured to receive haptics of an intraocular lens,
   wherein the ring-shaped flexible component is disposed around outer circumference of the circumferential wall of the ring-shaped rigid component,
   wherein the ring-shaped flexible component is configured to flex away from the ring-shaped rigid component when ciliary muscles are relaxed and zonules are tense,
   wherein a maximum thickness of the distal end of the ring-shaped rigid component is less than a maximum thickness of the proximal end of the ring-shaped rigid component.

2. The device of claim 1, wherein the plurality of markers is a guide for a toric lens alignment.

3. The device of claim 1, wherein said ledge has a width of about 0.1 mm to about 1 mm.

4. The device of claim 1, wherein said ring-shaped rigid component is substantially perpendicular to the anterior surface of the natural lens capsule.

5. The device of claim 1, wherein said ring-shaped flexible component is configured to flex toward the rigid component when the ciliary muscles are contracted and the zonules are relaxed.

6. The device of claim 1, wherein said gaps each have a width of about 0.1 mm to about 5 mm.

7. The device of claim 1, wherein said ring-shaped rigid component and said ring-shaped flexible component form an angle of about 2 degrees to about 90 degrees when fitted inside the natural lens capsule.

8. A prosthetic capsular device for flexibly restoring tension for a natural lens capsule after a cataract surgery, the device comprising a housing configured to receive an intraocular lens (IOL), the housing consisting of:
   a ring-shaped rigid component comprising:
      a distal end with a thickness of about 0.1 mm to about 0.5 mm, the distal end sized and configured to be disposed in a supporting relationship with an anterior surface of the natural lens capsule;
      an anterior central opening defined at said distal end, the anterior central opening having a perimeter capable of allowing insertion of an intraocular lens;
      a proximal end with a thickness of about 0.2 mm to about 1 mm, the proximal end comprising a capsular-engaging surface sized and configured to be disposed in a supporting relationship with a posterior surface of the natural lens capsule and configured to be disposed against a Wieger's ligament of the eye;
      a ledge formed from a top of the distal end of the rigid component, said ledge comprising a capsular-engaging top surface and a plurality of markers disposed on said top surface; and
      a circumferential wall extending from said proximal end to said distal end;
   a ring-shaped flexible component substantially concentric with said rigid component with a thickness of about 0.05 mm to about 0.75 mm that is less than the thickness of the distal end of the rigid component or the thickness of the proximal end of the rigid component, the ring-shaped flexible component defining a capsular-engaging circumferential wall sized and configured to flexibly fit against an inner surface of the natural lens capsule, said ring-shaped flexible component comprising:
      a proximal end formed on an outer surface of the proximal end of the rigid component;
      a distal end extending anteriorly and away from said rigid component, said distal end being a free end; and
      a plurality of gaps disposed around a circumference of the ring-shaped flexible component configured to improve flexibility; and
   a groove formed on an inner surface of the rigid component configured to receive haptics of an intraocular lens,
   wherein the ring-shaped flexible component is disposed around outer circumference of the circumferential wall of the ring-shaped rigid component,
   wherein the ring-shaped flexible component is configured to flex away from the ring-shaped rigid component when ciliary muscles are relaxed and zonules are tense, and configured to flex toward said ring-shaped rigid component when the ciliary muscles are contracted and the zonules are relaxed,
   wherein a maximum thickness of the distal end of the ring-shaped rigid component is less than a maximum thickness of the proximal end of the ring-shaped rigid component.

9. The device of claim 8, wherein the plurality of markers is a guide for a toric lens alignment.

10. The device of claim 8, wherein said gaps each have a width of about 0.1 mm to about 5 mm.

11. The device of claim 8, wherein said ledge has a width of about 0.1 mm to about 1 mm.

12. The device of claim 8, wherein said ring-shaped rigid component is substantially perpendicular to the anterior surface of the natural lens capsule.

13. The device of claim 8, wherein said ring-shaped rigid component and said ring-shaped flexible component form an angle of about 0 degree to about 90 degrees when disposed inside the natural lens capsule.

* * * * *